United States Patent
Wake et al.

(10) Patent No.: US 7,155,274 B1
(45) Date of Patent: Dec. 26, 2006

(54) OPTICAL COMPUTED TOMOGRAPHY SCANNER FOR SMALL LABORATORY ANIMALS

(75) Inventors: Robert H. Wake, Cooper City, FL (US); Brian Hummer, Pembroke Pines, FL (US); Gary M. Becker, Boca Raton, FL (US); Steve L. Ponder, Fort Lauderdale, FL (US); Vince Magraner, Miami, FL (US)

(73) Assignee: Imaging Diagnostic Systems, Inc., Plantation, FL (US)

( * ) Notice: Subject to any disclaimer, the term of this patent is extended or adjusted under 35 U.S.C. 154(b) by 563 days.

(21) Appl. No.: 10/717,969

(22) Filed: Nov. 21, 2003

(51) Int. Cl.
*A61B 6/00* (2006.01)

(52) U.S. Cl. ............ 600/476; 600/407; 600/425; 5/601; 5/611; 378/4; 378/6

(58) Field of Classification Search ........ 600/425, 600/476, 407, 415; 5/601, 611; 378/4, 6, 378/21, 23, 27, 195, 204, 208, 209; 250/337
See application file for complete search history.

(56) References Cited

U.S. PATENT DOCUMENTS

| | | | |
|---|---|---|---|
| 5,491,084 | A | 2/1996 | Chalfie et al. |
| 5,650,135 | A | 7/1997 | Contag et al. |
| 6,217,847 | B1 | 4/2001 | Contag et al. |
| 6,232,523 | B1 | 5/2001 | Tan et al. |
| 6,235,967 | B1 | 5/2001 | Tan et al. |
| 6,235,968 | B1 | 5/2001 | Tan et al. |
| 6,251,384 | B1 | 6/2001 | Tan et al. |
| 6,615,063 | B1 | 9/2003 | Ntziachristos et al. |
| 6,754,520 | B1 * | 6/2004 | DeSilets et al. ............ 600/415 |
| 2002/0013954 | A1 | 1/2002 | Yang et al. |
| 2002/0026649 | A1 | 2/2002 | Tan et al. |
| 2002/0114765 | A1 | 8/2002 | Grable et al. |
| 2003/0031628 | A1 | 2/2003 | Zhao et al. |
| 2003/0059400 | A1 | 3/2003 | Szalay |
| 2003/0065268 | A1 | 4/2003 | Chen et al. |
| 2003/0088885 | A1 | 5/2003 | Yang et al. |
| 2003/0161788 | A1 | 8/2003 | Zhao et al. |
| 2004/0057557 | A1 * | 3/2004 | Nafstadius ............ 378/209 |
| 2004/0089817 | A1 | 5/2004 | Long et al. |

FOREIGN PATENT DOCUMENTS

| | | |
|---|---|---|
| WO | WO 97/18841 | 5/1997 |
| WO | WO 98/49336 | 11/1998 |
| WO | WO 03/006069 | 1/2003 |
| WO | WO 03/0220042 | 3/2003 |

* cited by examiner

*Primary Examiner*—Brian L. Casler
*Assistant Examiner*—Jacqueline Cheng
(74) *Attorney, Agent, or Firm*—Shlesinger, Arkwright & Garvey LLP

(57) ABSTRACT

An optical CT scanner for small laboratory animals comprises a housing having a vertical through opening through which a test subject is passed through during a scanning session, the housing including a peripheral slot disposed transversely through the perimeter of the opening; a movable horizontal table disposed through the opening, the table being split with a horizontal slot aligned with the peripheral slot; a scanning head rotatable about the opening, the scanning head including a light beam directed toward the peripheral slot, the scanning head including a plurality of collimators directed toward the peripheral slot, the scanning head including a plurality of main photodetectors to detect the light beam after passing through the test subject and the collimators; a perimeter photodetector adapted to provide perimeter data of the test subject during a scanning session; an electrical circuit to amplify and digitize the output from the photodetectors; and a first computer programmed to reconstruct an image of the test subject from the output of the circuit.

18 Claims, 9 Drawing Sheets

OPTICAL COMPUTED TOMOGRAPHY SCANNER FOR SMALL LABORATORY ANIMALS

FIELD OF THE INVENTION

The present invention relates generally to an optical computed tomography (CT) scanner and specifically to an optical CT scanner for scanning small laboratory animals, such as nude mice carrying cancer cells with fluorophore, such as green fluorescent protein (GFP).

BACKGROUND OF THE INVENTION

Fluorescence is often used in biology and particularly in optical microscopy for tissue identification. A fluorophore chosen for its abilities to bind to or 'tag' a specific type of tissue is introduced into the sample being interrogated. When the sample is illuminated by light at the excitation wavelength of the fluorophore, the tissue tagged by the fluorophore will emit light at the fluorophore's emission wavelength, thereby allowing optical detection of that tissue's presence and evaluation of the tissue's distribution within the sample.

A sizeable industry exists to support fluorescent optical microscopy. Several microscope manufacturers (e.g. Nikon Zeiss, Olympus) offer adapters for their instruments that allow fluorescent microscopy using the microscopes' existing light sources. Biochemical suppliers such as Fluka BioChemika, Molecular Probes, Fuji Photofilm and Sigma-Aldrich supply scores of different fluorophores that are designed with specific optical and biochemical properties. Optics companies such as Omega Optical, Barr Associates, and Semrock supply optical filters for both the excitation and fluorescent emission wavelengths, allowing customization of microscopy equipment for specific fluorophores.

An extension of the concept of fluorescent microscopy is to image tissue-bound fluorophores in animals in vivo, or immediately post mortem, to ascertain the distribution of the tagged tissue. In this application, typically a white-light source is filtered with an excitation filter appropriate to the fluorophore, and a video camera, usually a CCD camera, views the test subject through an appropriate fluorescence emission filter. The camera produces a two-dimensional image that is a projection of the fluorophore's distribution onto a plane, much like a conventional two-dimensional x-ray. Although these two-dimensional images show the distribution of the fluorophore, accurate estimation of the quantity of tagged tissue within the sample (e.g. the volume of a tumor) is difficult without using actual three-dimensional fluorescent images of the sample. Several companies produce 2-D fluorescence imaging systems, notably Xenogen's IVIS® Imaging System, Berthold Technologies' NightOWL LB98, and ART Advanced Research Technologies, Inc.'s SAMI. None of these systems, however, show volumetric data that can allow quantitative estimation of tissue volumes.

Prior art fluorescent imaging systems, such as those described above, are used in cancer research to evaluate anticancer treatments in nude mice. These hairless mice carry a recessive gene that inhibits the development of the thymus gland. The mice are unable to generate mature T-lymphocytes and therefore are unable to mount most types of immune responses, including antibody formation and rejection of transplanted tissues. Cancerous allografts and xenografts are readily accepted and nurtured by the mice, making them excellent vehicles for the study of human cancers and their reactions to different treatments. Treatment efficacy is monitored by injecting a tumor-bearing nude mouse with a cancer-specific fluorophore and then tracking the change in tumor size with a fluorescent imaging system.

A technique developed in the mid-1990's creates cancer cells that are genetically altered to fluoresce, obviating an injected fluorophore. Green fluorescent protein (GFP), which is produced by certain jellyfish, emits green light when exposed to certain wavelengths of blue light. By 'transfecting' the appropriate DNA segment from these jellyfish into other cells, the cells are made to express GFP. In cancer research, the cancer cells are transfected with the GFP gene, and the progression of the tumor or its metastases can be monitored noninvasively by its GFP fluorescence using fluorescence imaging.

Recently, cells have been genetically modified to express fluorophores at other wavelengths (particularly by the Clontech division of Becton Dickinson), but GFP-expressing cells are much more widely used than any of these new cells.

Human cancer cells are being grown that are transfected with the GFP gene. These cancer cells are transplanted into nude mice, which do not reject the cancer, rather they nourish the cancer, allowing testing of anticancer treatments. The progression of the cancer or its metastases can be imaged with fluorescence of the GFP.

OBJECTS AND SUMMARY OF THE INVENTION

It is an object of the present invention to provide an optical CT scanner for small laboratory animals injected with a cancer-specific fluorophore, such as green fluorescent protein (GFP), to monitor the progression of the tumor so as to evaluate the efficacy of cancer treatment being studied.

If is another object of the present invention to provide an optical CT scanner that can image both attenuation and fluorescence distributions in small laboratory animals injected with a fluorophore, thereby to locate and quantify the volumetric size of tumors growing in these animals for research purposes.

If is yet another object of the present invention to provide an optical CT scanner made to a relatively small size, for example, 400 mm cube, so as to be conveniently situated within a typically crowded laboratory setting.

In summary, the present invention provides an optical CT scanner for small laboratory animals, comprising a housing having a vertical through opening through which a test subject is passed through during a scanning session, the housing including a peripheral slot disposed transversely through the perimeter of the opening; a movable horizontal table disposed through the opening, the table being split with a horizontal slot aligned with the peripheral slot; a scanning head rotatable about the opening, the scanning head including a light beam directed toward the peripheral slot, the scanning head including a plurality of collimators directed toward the peripheral slot, the scanning head including a plurality of main photodetectors to detect the light beam after passing through the test subject and the collimators; a perimeter photodetector adapted to provide perimeter data of the test subject during a scanning session; an electrical circuit to amplify and digitize the output from the photodetectors; and a first computer programmed to reconstruct an image of the test subject from the output of the circuit.

These and other objects of the present invention will become apparent from the following detailed description.

BRIEF DESCRIPTIONS OF THE DRAWINGS

DETAILED DESCRIPTION OF THE INVENTION

Figure 1:
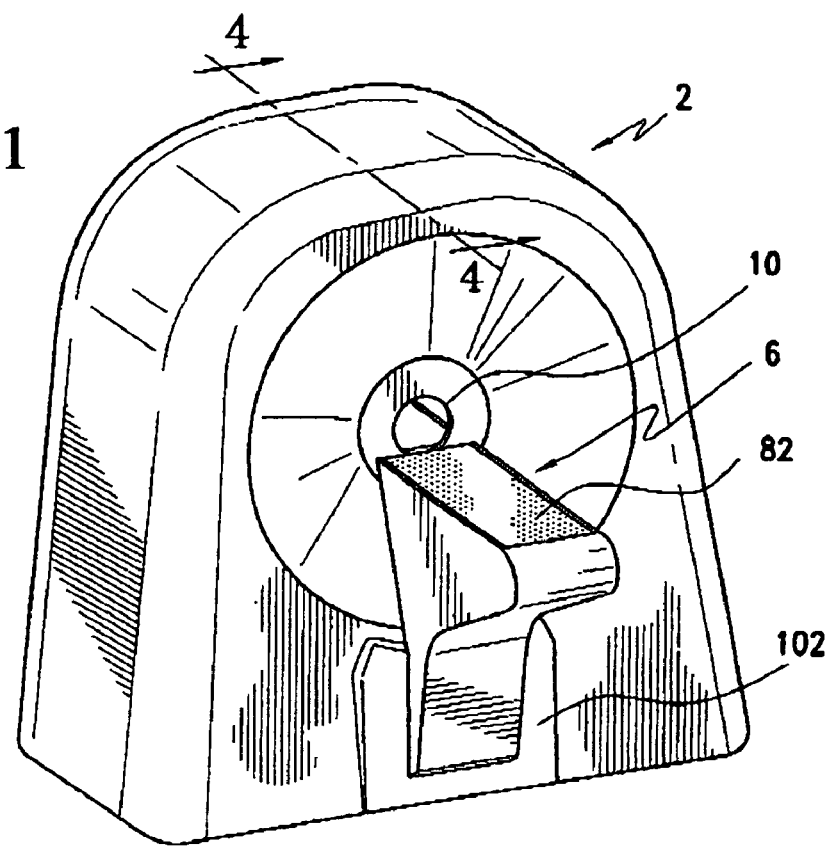
FIG. 1 is a front perspective view of an optical CT scanner for small laboratory animals made in accordance with the present invention.
Figure 2:
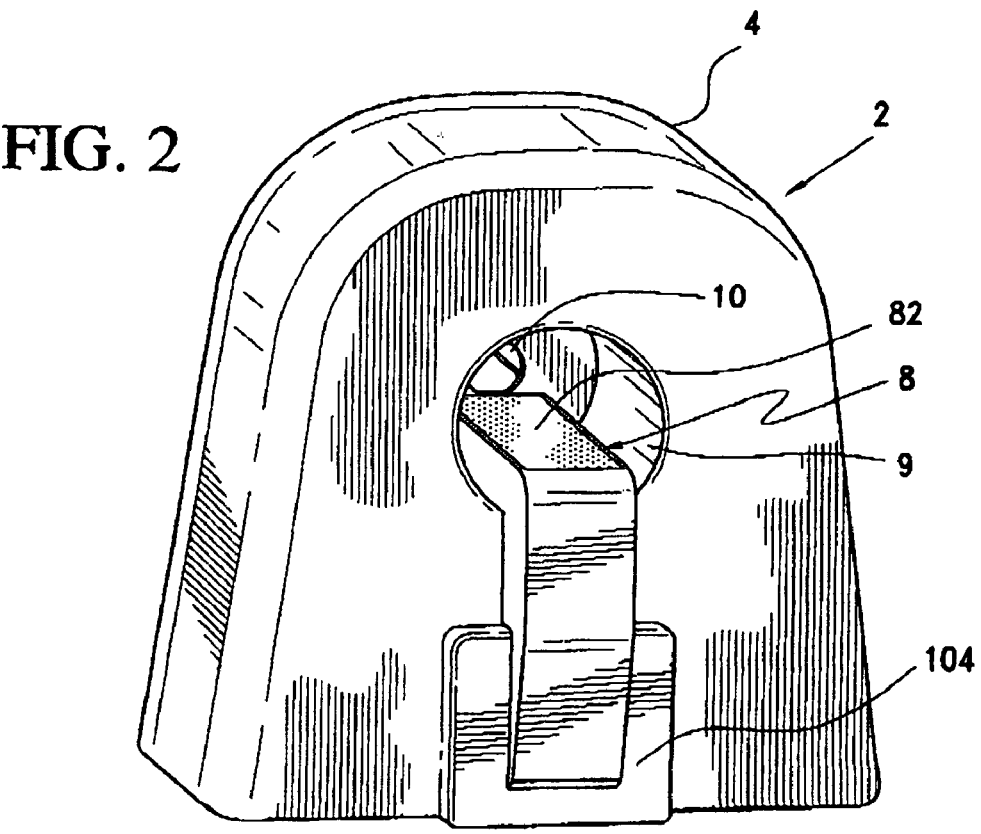
FIG. 2 is a rear perspective view of FIG. 1.
Figure 3:
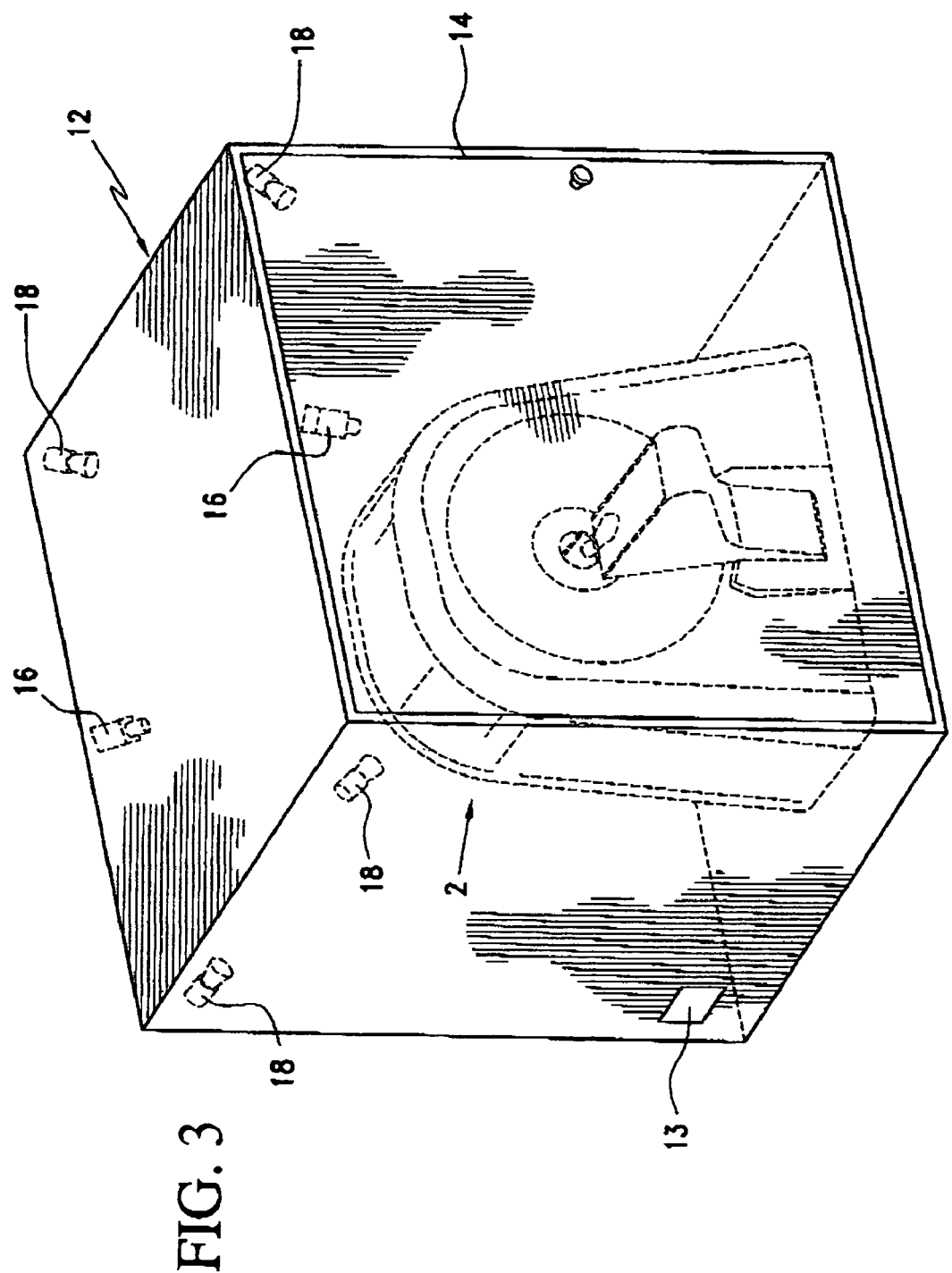
FIG. 3 is the scanner of FIG. 1 shown enclosed within a light-tight enclosure.

An optical computed tomography scanner 2 made in accordance with the present invention is disclosed in FIGS. 1 and 2. The scanner 2 includes a housing 4 and horizontal front and rear tables 6 and 8, respectively. The housing has a vertical opening 10 to allow the test subject to go from the front table 6 to the rear table 8 during scanning, as will be further described below. The housing 4 includes a well 9 having a bottom at which the opening 10 is disposed. The well 9 advantageously allows the user to observe the test subject as it progresses toward the rear table 8.

The scanner 2 is placed within a light-tight enclosure 12 to prevent room light from contaminating the light transmitted through the test subject by the scanner. The enclosure 12 is provided with light-tight door 14 to provide access to the scanner 2.

Video cameras 16 are provided within the enclosure 12 to provide remote monitoring of the test subject during the scanning period. Light fixtures 18 provide illumination within the enclosure 12 not detectable by the scanner, such as yellow or red light. The enclosure 12 is advantageously small, for example about 400 mm cube, so as to not occupy so much space in a crowded laboratory where space is a premium. A light-tight access port 13 for cables and other lines is provided.

Figure 4:
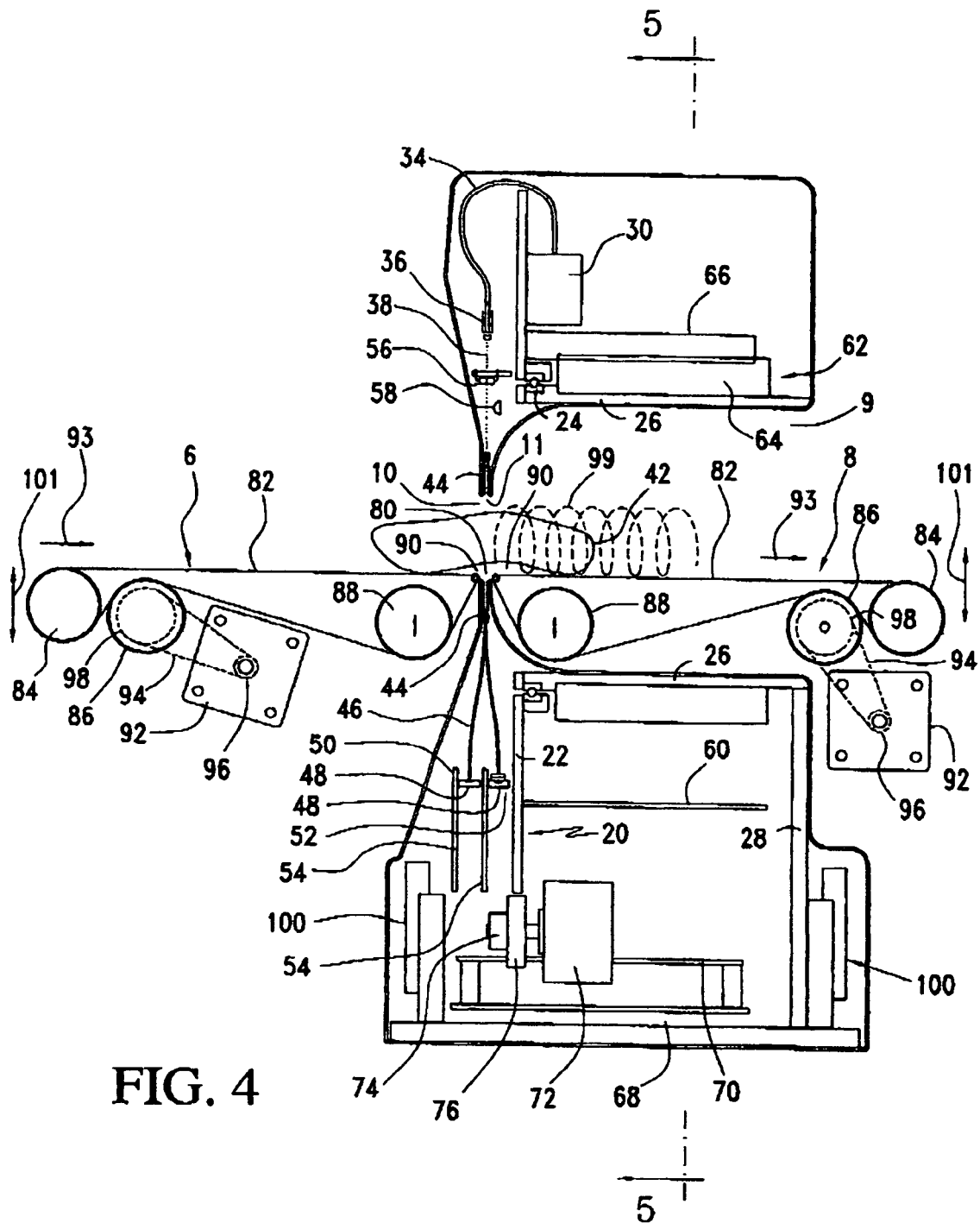
FIG. 4 is a cross-sectional view taken along line 4—4 of FIG. 1, with portions shown schematically.
Figure 5:
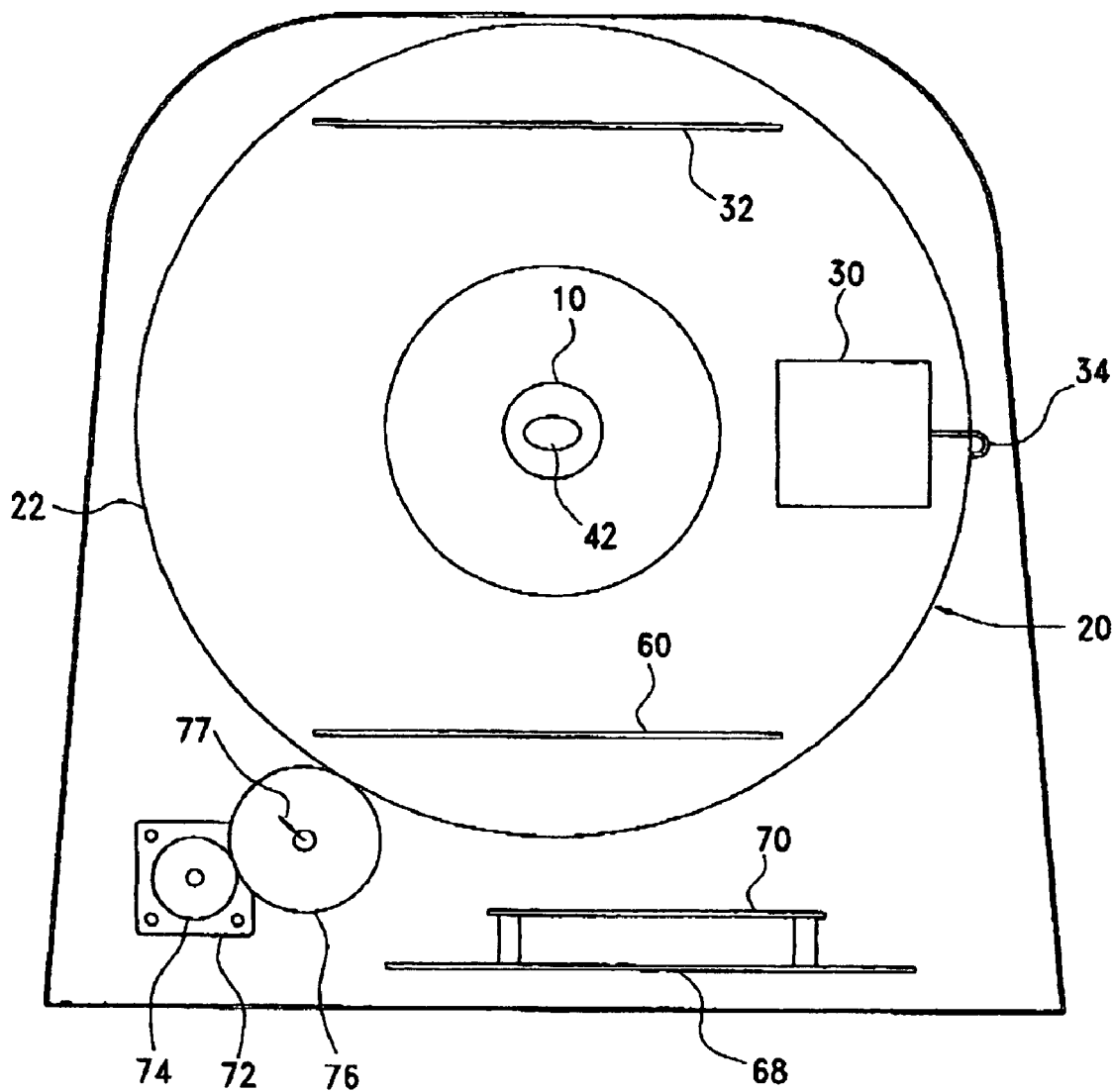
FIG. 5 is a schematic view taken along line 5—5 of FIG. 4.

Referring to FIGS. 4 and 5, the scanner 2 comprises a vertically rotating scanning head 20 comprising a rotating plate 22 mounted on a ball bearing 24, which mounts on a stationary hub 26 supported by a vertical structure 28. Laser diode 30 and its controller 32 are carried by the rotating plate 22. The output of the laser diode 30 may be connected to an optic fiber 34 to a collimator 36 to project a parallel beam of light 38 across the scanning aperture 10 to illuminate a test subject 42. Other methods of aiming the laser output to the collimator 36, such as by mirrors, may be used. The laser beam is passed through an annular gap 11 in the housing 4 in the periphery of the opening 10.

Figure 8:
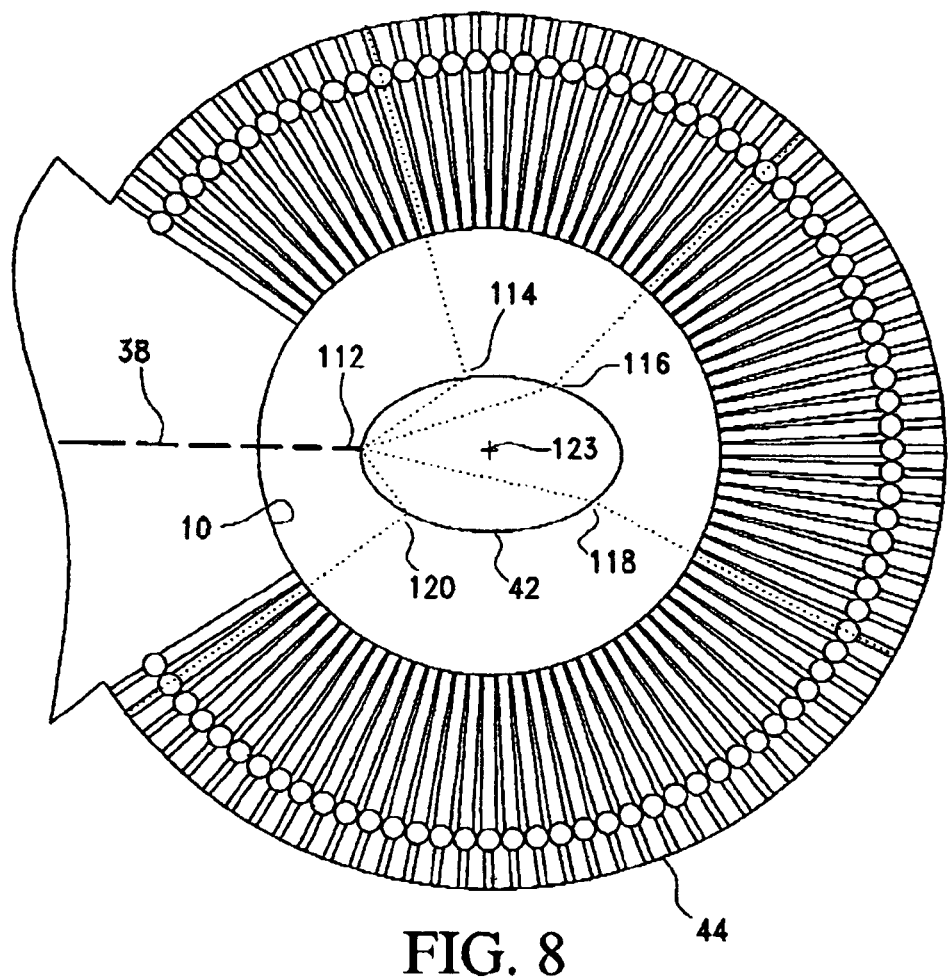
FIG. 8 is an enlarged plan view of the collimator assembly, showing how a laser beam entering a test subject might exit and be picked up by the collimators.

The rotating plate 22 also carries a plurality of collimators 44 (see FIG. 8). Each collimator 44 is preferably connected by a respective optic fiber 46 to a respective photodetector 48. However, each photodetector 48 may be directly coupled to the end of its respective collimator 44, without using an optic fiber. The optic fibers 46 and the photodetectors 48 are also carried by the rotating plate 22. The photodetectors 48 are preferably arranged in first and second arrays, where the first array 50 is above or to the left of the second array 52. The collimators 44 can then be assigned alternately between the first and second arrays of photodetectors, so that the first array 50 may be assigned for attenuation light and the second array 52 for fluorescent light. The photodetectors 48 are carried by the rotating plate 22.

There are preferably 84 collimators, spaced about 3.5° from each other, for a total 290° arc coverage. The collimators 44 and the laser beam 38 are aligned on a scanning plane through the annular gap 11.

Photodetector amplifiers 54, two CCD cameras 56 and a reference diode 58 are also carried by the rotating plate 22. Data acquisition controller 60 is also carried by the rotating plate 22.

A slip ring 62, comprising a stationary rotor 64 and a rotating stator 66, conveys electrical power and signals to and from the rotating electronics of the scanning head 20 to a stationary date acquisition module 68 and a stationary embedded computer 70.

The rotating plate 22 is driven by a stepping motor 72 via a drive wheel 74 and an idler wheel 76, which is spring loaded as schematically indicated at 77. Advantageously, the speed ratio between the drive wheel 74 and the rotating plate 22 remains the same even when the idler wheel 76 wears out. The idler wheel 76 is preferably rubber surfaced for good contact with the wheels 74 and 22, both of which are preferably made of metal.

Referring again to FIG. 4, the front table 6 is separated with a small air gap 80 from the rear table 8. The gap 80 advantageously allows the emitted light from the test subject 42 to reach the collimators 44 and the respective photodetectors without further attenuation. The gap 80 is aligned with the scanning plane and the annular gap 11 at the opening 10.

The front and rear tables 6 and 8 are functionally identical, each comprising an endless conveyor belt 82 passing over three large pulleys 84, 86, and 88 and a small diameter pulley 90. The conveyor belt 82 is a thin, preferably non-stretching materials, such as KAPTON or MYLAR. The small diameter pulley 90 is located adjacent the gap 80, thereby advantageously allowing the gap 80 to be minimized preferably to a few millimeters. The small diameter pulley 90 can be a rotating pulley with small bearings, such as jeweled bearings, or can be highly polished stationary round pin that the conveyor belt 82 slides on, or other standard structures. The conveyor belt 82 is driven by the pulley 86, which itself is driven from a stepping motor 92 by a toothed belt 94 via toothed-belt pulleys 96 ad 98. The pulley 84 acts at the end of the respective table and the pulley 88 is a tensioner, moving vertically, either spring-loaded or relying on gravity or some standard means to tension the conveyor belt 82. The top, outside surface of the conveyor belt 82 has a matte finish to better support the test subject, provide more friction against the driver pulley 86 and to minimize stray light reflection from being picked up by the photodetectors.

The lower, inner side of the conveyor belt 82 is preferably smooth or shiny to minimize friction against the pulleys 84, 88 and 90.

The stepping motors 92 that drive the conveyor belt 82, and the stepping motor 72 that drives the scanning head 20 together provide a precise screw thread or helical pattern 99 for scanning the test subject 42. As the scanning head 20 rotates continuously during scanning, generally indicated at 91 (see FIG. 6), for example, at a rate selectable from about 5–20 sec./revolution, the tables at the same time move forward at identical rate, generally indicated at 93, for example, at a selectable speed from about 0.05 mm–5 mm/sec., giving a minimum slice thickness at the fastest orbit time of 0.25 mm.

The front and rear tables 6 and 8 are mounted on respective vertical lift mechanisms 100. The front and rear tables 6 and 8 are raised or lowered synchronously, generally indicated at 101, remaining at the same height at all times. The tables 6 and 8 are raised or lowered to align the centerline of the test subject 42 with the center of rotation of the scanning head 20. The lift mechanisms 100 are driven from the data acquisition module 68 under the control of the embedded computer 70. The lift mechanisms 100 is of standard construction and may include vertical slides driven by a linear actuator comprising a lead screw powered by a stepping motor. Since the CCD cameras 56 measure the perimeter of the test subject during scanning, the height of the tables may be adjusted automatically and continuously during scanning to keep the test subject's centerline on the scanning head's centerline.

It should be understood that, although not shown, it is standard construction to provide the appropriates support structures to support the endless conveyor belts 82 and the associated pulleys and stepping motor with the vertical lift mechanisms 100, such as that shown schematically at 102 for the front table 6 and 104 for the rear table 8 in FIGS. 1 and 2.

Figure 7:
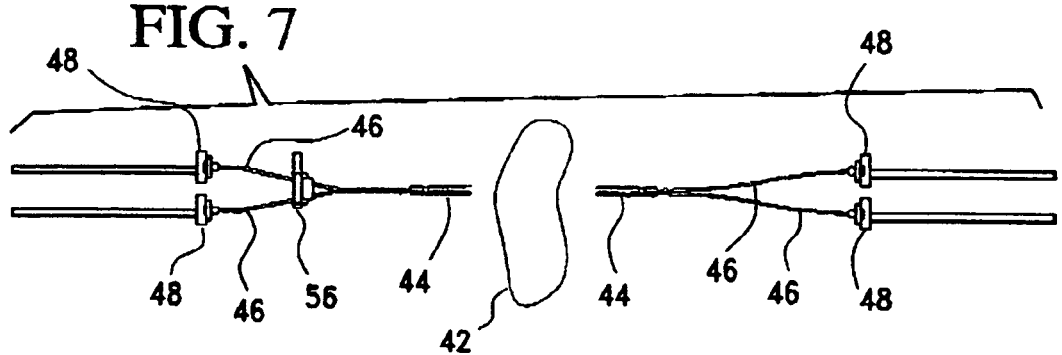
FIG. 7 is a schematic view along the scanning plane of the scanner head of FIG. 6.
Figure 6:
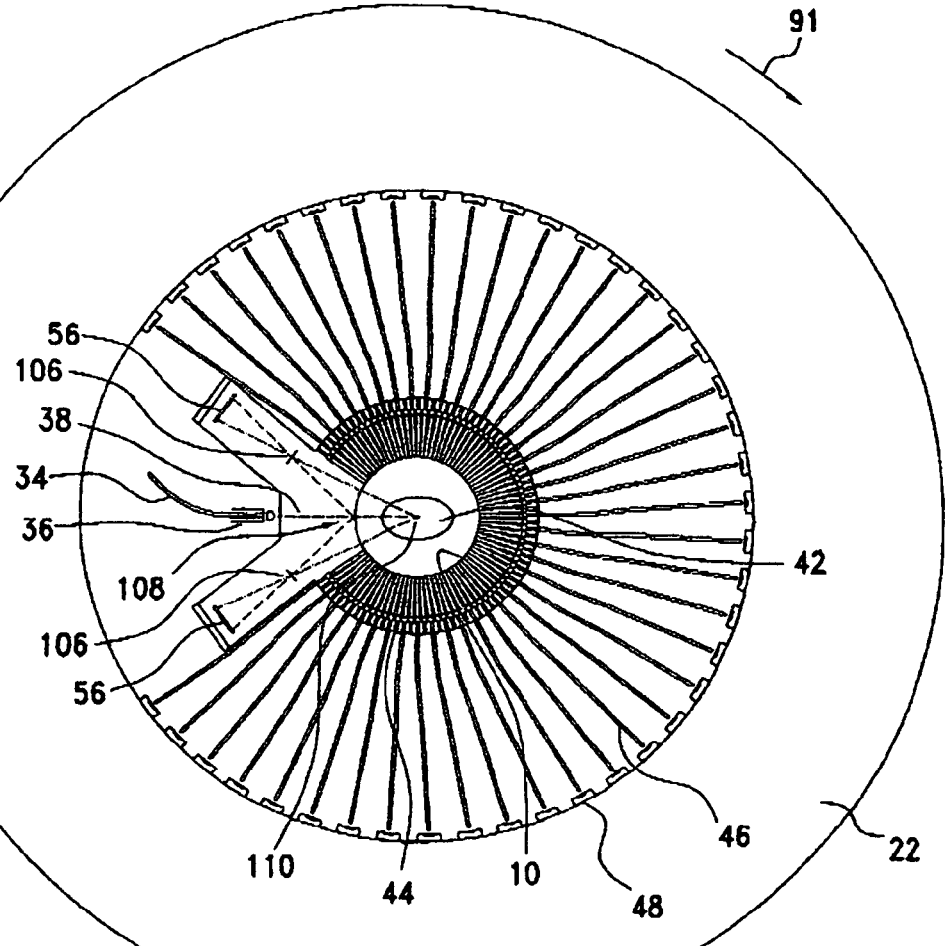
FIG. 6 is a partial front view of a vertical scanning head of the scanner of FIG. 1, with portions omitted, showing the arrangement of the collimators, photodetectors, the laser beam and the CCD cameras used for generating image data.

Referring to FIGS. 6 and 7, the CCD cameras 56 image the laser beam landing spot on the test subject through respective vertical slits 106. The CCD cameras 56 are linear cameras, preferably 128×1 pixels, which image the lateral position of the laser beam landing spot as the distance to the surface of the test subject changes. For example, as the landing spot moves from a maximum position at 108 at the edge of the opening 10, to a minimum position at 110 at the center of rotation of the rotating plate 22, the spot imaged by the CCD camera 56 will move from one end of the linear camera to the opposite end, each position in between representing a specific perimeter point on the test subject. The perimeter of the test subject is thus obtained during scanning, as disclosed in U.S. Pat. No. 6,044,288. The vertical slits 106, which are disposed perpendicular to the scanning plane (parallel to the plane of FIG. 6), is advantageously used in lieu of a lens, to focus the laser spot on the CCD cameras. The vertical slits 106, approximately 0.1 mm, will act as pinhole lens in the plane of the collimators 44, and like a pinhole lens, will have a large depth-of-field. Being a slit perpendicular with the scanning plane, it is advantageously insensitive to aiming errors in that direction. Each slit 106 will take the landing spot and project it into a short vertical line intersecting the horizontal line of the 128×1 pixels of the respective CCD camera 56.

Figure 9:
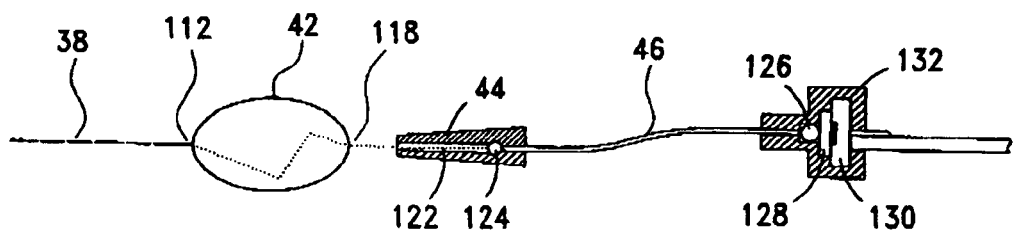
FIG. 9 is a schematic view taken along the scanning plane of FIG. 8, showing a typical light path taken by the laser beam impinging the test subject.

Referring to FIGS. 8 and 9, the test subject 42 is illuminated by the laser beam 38 at point 112. The laser light scatters within the test subject and is emitted from the surface of the test subject 42, for example at points 114, 116, 118 and 120, which are then received by the respective collimators 44. During a scan, the assembly of collimators 44 continuously rotates while at the same time the test subject 42 moves through the opening 10 of the scanning aperture.

The laser diode 30 preferably has a beam diameter of about 0.3 mm–0.6 mm. at the center of rotation.

Referring to FIG. 9, the light exiting the test subject 42, for example at point 118, passes into a rectangular channel 122 of the collimator 44. The centerline through the channel 122 and the laser beam 38 are preferably coplanar and preferably directed toward the center 123 of rotation of the scanning head. The collimator 44 preferably tapers in the scanning plane. At the end of the rectangular channel 122, the light strikes a lens 124, preferably a ball lens made of sapphire. The lens 124 focuses the light into the optical fiber 46, which passes the light with minimal attenuation to a lens 126, preferably a ball lens made of sapphire. The lens 126 collimates the light into an approximately parallel beam for passing through a filter 128 before striking a photodetector 130, where the light is converted to an electrical charge and is then amplified. An opaque housing 132 contains the lens 126, the filter 128 and the photodetector 130.

The filter 128 is chosen for the fluorophore to be used in the test subject. For GFP, the filter 128 will pass light in the range 500–560 nanometers, with minimal transmission at the laser's wavelength of 440–495 nanometer. Preferably, every other collimator 44 will be filtered for fluorescence, and the rest will be assigned to measuring attenuation at the laser wavelength. The attenuation collimators are filtered to reject long wavelengths beyond 550 nanometers so that yellow and red lighting can be used to illuminate the enclosure 12 and not contaminate the scan data. The lighting in the scanning enclosure 12 advantageously allows the operator to monitor the status of the test subject via the video cameras 16 placed inside the enclosure 12.

Attenuation data may be useful for providing anatomical landmarks within the test subject that otherwise would not be visible with fluorescence data. By superimposing the fluorescence image over the attenuation image, the fluorescence image may be properly located within the test subject.

Other assignments of the collimators 44 can be used. For example, the scanner 2 may be provided with two lasers at different wavelengths for exciting different fluorophores. In this case, one set of collimators can be assigned, with the appropriate filter, to detect fluorescence at one wavelength, another set for fluorescence at another wavelength and the rest for attenuation at one of the laser's wavelengths.

The assembly of collimators 44 preferably has 84 channels, with septa between channels as thin as 0.1 mm. The collimator channel 122 is preferably rectangular in cross-section. The collimator assembly is preferably fabricated by stereo lithography, a standard prototyping technology where the part is built-up additively in very thin layers with no constraint on geometry and adequate tolerances.

Figure 10:
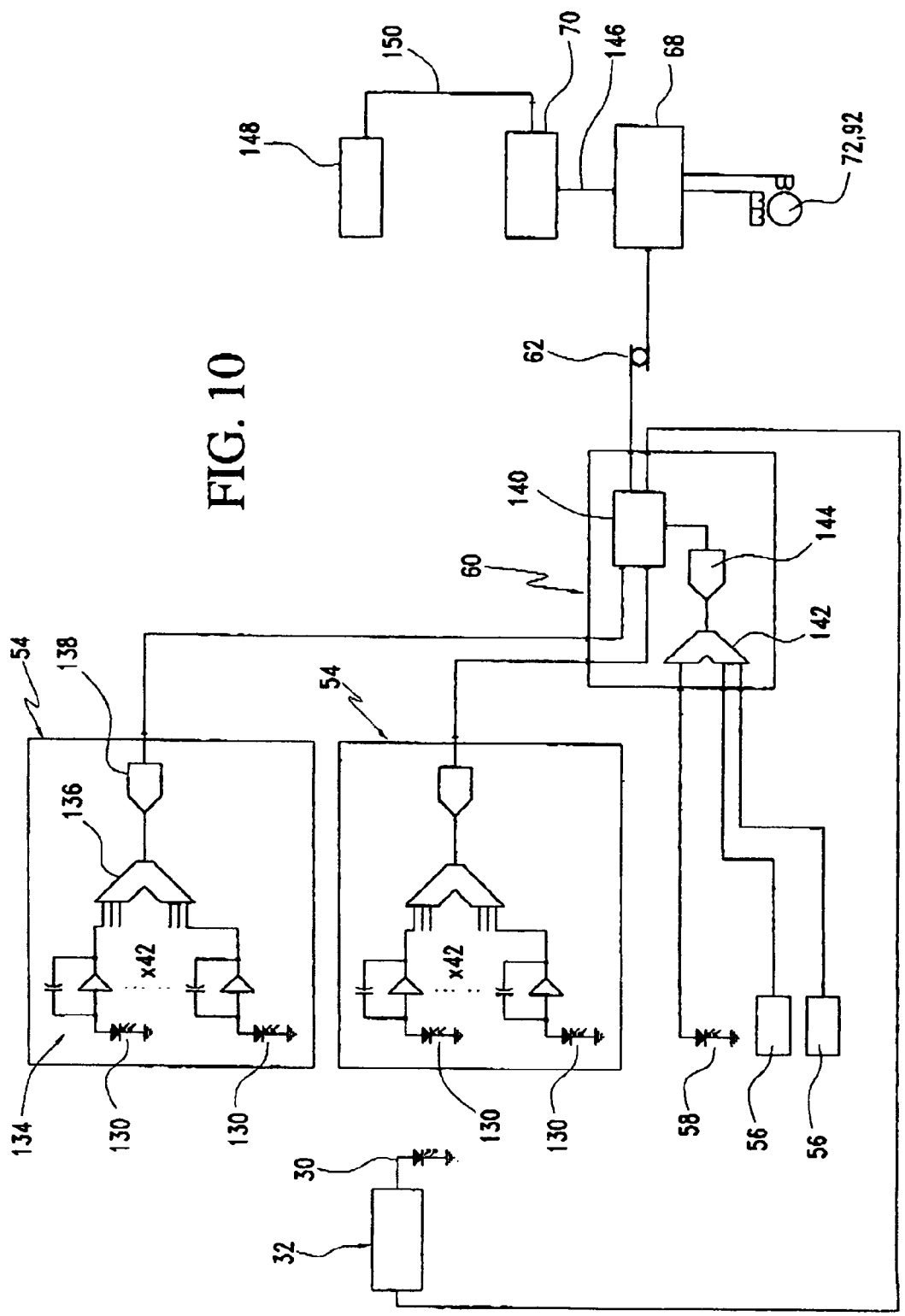
FIG. 10 is a schematic diagram of the electronic system of the scanner of FIG. 1.

Referring to FIG. 10, an electrical schematic of the scanner 2 is disclosed. The laser diode 30 emits light that is attenuated and scattered by the test subject 42 and received by the photodiodes 130, which is connected to a switch integrating operational amplifier 134. The timing of the integration period effects a gain control, as disclosed in U.S. Pat. No. 6,150,063. Each switch integrating operational amplifier 134 is selected by a multiplexer 136 and presented to an analog-to-digital converter 138, where the output of the amplifier is digitized. The switched amplifier circuits 134 are preferably grouped to correspond to the first and second arrays of photodetectors 50 and 52 for the embodiment of 84 photodetectors.

The timing and control of the multiplexer 136 and the converter 136 is provided by a field programmable gate array (FPGA) 140 located on the acquisition control module. The FPGA 140 controls the timing of the acquisition data, the CCD camera data and the reference detector data, all under the command of the embedded processor 70. The FPGA 140 arranges (packetize) and serializes these data for transmission to the data acquisition module 68. An example of the FPGA 140 is a Xilinx Spartan XCS40XL.

The reference photodiode 58 and the CCD cameras 56 connect to a multiplexer 142 where the output of each is selected and digitized by an analog-to-digital converter 144. The digital data is presented to the FPGA 140. The FPGA 140 serializes and de-serializes the digital data for transmission to the data acquisition module 68 over the slip ring 62.

The data acquisition module 68 controls the stepping motors 72 and 92 and the stepping motor for the lifting mechanisms 100. The data acquisition module 68 also buffers the acquisition data for the embedded processor 70.

The embedded processor 70, such as a PC/104 processor, controls the scanner operation and the collection of data. The embedded processor 70 communicates with the data acquisition module 68 via an ISA bus 146 (PC-80 bus). The embedded processor 70 uploads the acquisition data, performs some diagnostic functions and transmits the data to an operator's terminal 148 over a link 150, preferably a 100 Mbit Ethernet link. Other types may be used, such as USB2.0 or FIREWIRE. The use of an embedded processor 70 advantageously allows multiple scanners to be controlled, from a single operator's terminal.

The operator's terminal 148 consists of a standard personal computer, a video monitor, keyboard, mouse and printer. The terminal 148 is used to record information on the test subject, set scan parameters and acquire image data. It is also used to reconstruct attenuation and fluorescence volume images and display multiplanar and interactive 3-D representations of the volumes. Further, the terminal 148 is used to calculate and save measurements from the volumes and output selected data and images for report writing. The terminal 148 also backups reconstructed volumes, snapshots and measurements to a storage device, such as DVD-R. Diagnostics may also be performed by the terminal 148.

Figure 11:
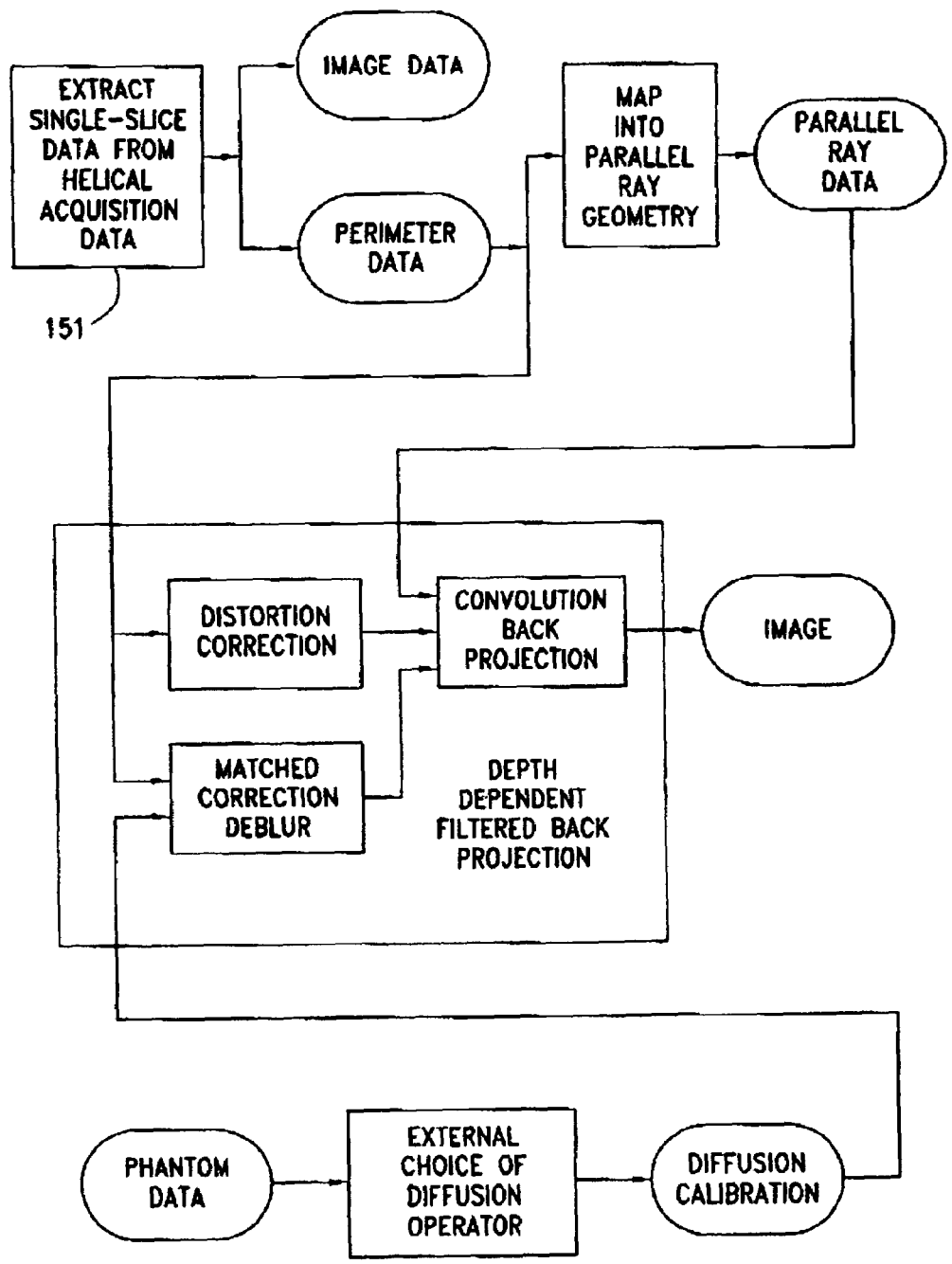
FIG. 11 is a block diagram of an algorithm used for image reconstruction.
Figure 12:
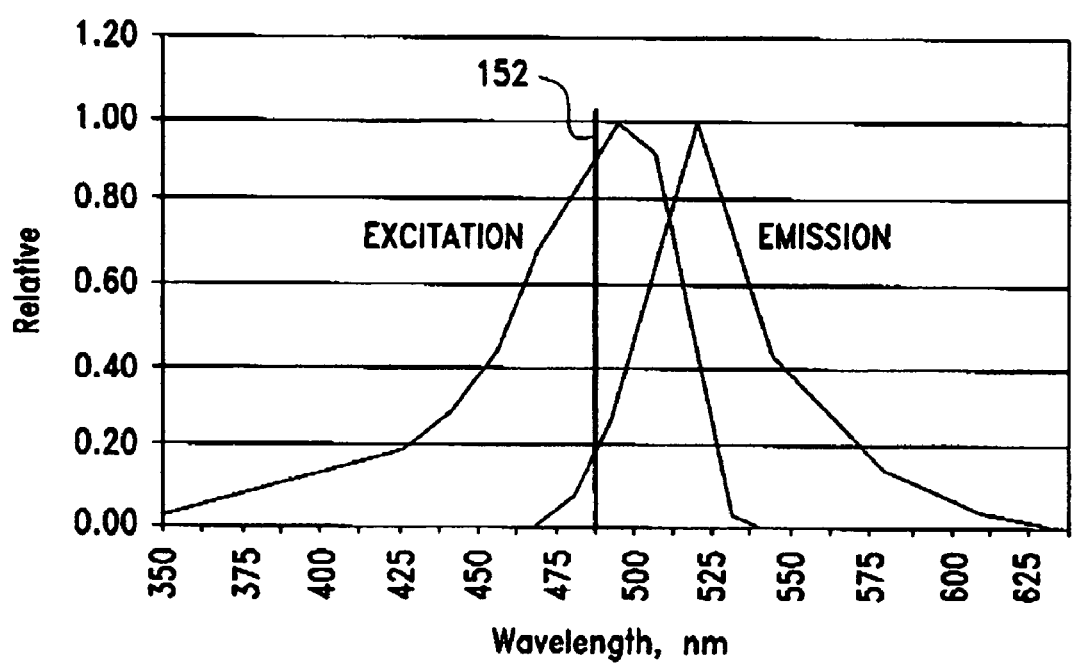
FIG. 12 is an example of the excitation and emission spectra of GFP.

Fluorescence and absorption image reconstructions are accomplished with a filtered back projection algorithm as shown in FIG. 11. The algorithm at 151 extracts image acquisition data and CCD camera data from the helical set and create an artificial slice for reconstruction which is then used by the rest of the algorithm in a manner disclosed in U.S. Pat. No. 6,139,958.

The PC in the terminal 148 can also connect to the video cameras 16 in the enclosure 12, preferably via USB 2.0 to display live images of the test subject during the scanning process. Since the test subject must remain motionless, the operator must know that the anesthetic has not worn off.

Referring to FIG. 11, an example of excitation emission spectra for GPF is disclosed. The vertical line 152 represents a 488 nm laser which will excite the GFP at close to its maximum efficiency.

The test subject may be a nude mouse transfected with GFP. The scanner 2, equipped with the laser diode at about 440–495 nm, and the collimators filtered with bandpass filters in the range of 500–560 nm, will collect data over time on the growth of any tumor growing anywhere, including in the abdomen and lung, in the mouse that has been injected with GFP. The mouse is paralyzed and anaesthetized during the scanning process. A blind fold is placed over the mouse's eyes to protect them from the laser during the scanning process. The volume of the tumor can then be quantified, providing the researcher valuable information on the effectiveness of a drug under study.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. An optical CT scanner for small laboratory animals, comprising:
   a) a housing having a vertical through opening through which a test subject is passed through during a scanning session;
   b) said housing including a peripheral slot disposed transversely through the perimeter of said opening;
   c) a movable horizontal table disposed through said opening, said table being split with a horizontal slot aligned with said peripheral slot;
   d) a scanning head rotatable about said opening, said scanning head including a light beam directed toward said peripheral slot, said scanning head including a plurality of collimators directed toward said peripheral slot, said scanning head including a plurality of main photodetectors to detect said light beam after passing through the test subject and said collimators;
   e) a perimeter photodetector adapted to provide perimeter data of the test subject during a scanning session;
   f) an electrical circuit to amplify and digitize the output from said photodetectors; and
   g) a first computer programmed to reconstruct an image of the test subject from the output of said circuit.

2. An optical scanner as in claim 1, wherein:
   a) said housing includes a well having a bottom; and
   b) said opening is disposed at said bottom of said well.

3. An optical scanner as in claim 1, wherein:
   a) said table includes front and rear tables movable vertically synchronously.

4. An optical scanner as in claim 3, wherein:
   a) said front and rear tables each includes an endless belt; and
   b) said endless belts are driven synchronously with each other.

5. An optical scanner as in claim 1, wherein:
   a) said scanning head comprises a vertical plate rotatable about an axis through said opening; and
   b) said collimators, main photodetectors, light beam and perimeter detector are carried by said plate.

6. An optical scanner as in claim 1, wherein said scanning head comprises a plurality of optic fibers to transmit light from a respective collimator to a respective photodetector.

7. An optical scanner as in claim 1, wherein:
   a) said photodetectors comprises first and second arrays; and
   b) said first array is disposed above said second array.

8. An optical scanner as in claim 7 wherein:
   a) said first array is adapted for detecting attenuation light; and
   b) said second array is adapted for detecting fluorescent light emitted by green fluorescent protein within the test subject.

9. An optical scanner as in claim 1, wherein each of said collimators include a lens operably associated with a respective optic fiber.

10. An optical scanner as in claim 1, wherein each of photodetectors includes a lens operably associated with a respective optic fiber.

11. An optical scanner as in claim 1, wherein said collimators are arranged in an arc of about 290° around said opening.

12. An optical scanner as in claim 1, wherein said scanning head rotates continuously during scanning while said table moves forward, creating a helical scanning pattern around the test subject.

13. An optical scanner as in claim 1, wherein said table moves vertically during scanning.

14. An optical scanner as in claim 1, wherein:
a) said electrical circuit includes a plurality of switched amplifier circuits connected to respective photodetectors and an analog to digital converter (ADC) for digitizing the output of said switched amplifier circuits; and
b) a second computer disposed within said housing to control said switched amplifier circuits and said ADC.

15. An optical scanner as in claim 14, wherein said electrical circuit includes a slip ring to connect said second computer to said switched amplifier circuits and said ADC.

16. An optical scanner as in claim 1, wherein said perimeter photodetector is a CCD camera having a linear element.

17. An optical scanner as in claim 1, and further comprising a vertical slit to focus a landing spot of said laser beam on the test subject onto said perimeter photodetector.

18. An optical scanner as in claim 1, wherein said laser beam is generated by a laser diode.

* * * * *